(12) United States Patent
Nishimura (10) Patent No.: US 9,672,596 B2
(45) Date of Patent: Jun. 6, 2017

(54) IMAGE PROCESSING APPARATUS TO GENERATE A REDUCED IMAGE OF AN ENDOSCOPIC IMAGE

(71) Applicant: OLYMPUS CORPORATION, Tokyo (JP)

(72) Inventor: Hirokazu Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/209,356

(22) Filed: Jul. 13, 2016

(65) Prior Publication Data

US 2016/0321785 A1 Nov. 3, 2016

Related U.S. Application Data

(63) Continuation of application No. PCT/JP2015/060094, filed on Mar. 31, 2015.

(30) Foreign Application Priority Data

Mar. 31, 2015 (JP) ................. 2015-555491

(51) Int. Cl.
| | |
|---|---|
| G06K 9/00 | (2006.01) |
| G06K 9/40 | (2006.01) |
| G06K 9/32 | (2006.01) |
| G06T 3/40 | (2006.01) |
| G06T 5/20 | (2006.01) |
| G06T 5/00 | (2006.01) |
| A61B 1/00 | (2006.01) |

(52) U.S. Cl.
CPC ......... *G06T 3/4092* (2013.01); *A61B 1/0005* (2013.01); *A61B 1/00009* (2013.01); *G06T 5/002* (2013.01); *G06T 5/20* (2013.01); *G06T 2207/10068* (2013.01); *G06T 2207/20024* (2013.01); *G06T 2207/20182* (2013.01)

(58) Field of Classification Search
None
See application file for complete search history.

(56) References Cited

FOREIGN PATENT DOCUMENTS

| JP | 01270842 A | 10/1989 |
|---|---|---|
| JP | 2009218944 A | 8/1997 |
| JP | 2000-165664 A | 6/2000 |
| JP | 2002-077698 A | 3/2002 |
| JP | 2012-005044 A | 1/2012 |

OTHER PUBLICATIONS

International Search Report and Written Opinion dated Jul. 7, 2015 issued in PCT/JP2015/060094.
Japanese Office Action dated Jan. 19, 2016 issued in JP2015-555491.

*Primary Examiner* — Randolph I Chu
(74) *Attorney, Agent, or Firm* — Scully, Scott, Murphy & Presser, PC (57) ABSTRACT

A filtering unit applies a filter for suppressing a high-frequency component to a second image generated by performing image processing including at least enlargement processing on a first image captured by using an endoscope. An image reducing unit generates a third image by performing reduction processing on the second image to which the filter has been applied. A filter setting unit sets a characteristic of a filter based on information on a maximum frequency component that can be reproduced in at least the first image and information on a maximum frequency component that should be reproduced in the third image.

4 Claims, 9 Drawing Sheets

| IMAGE NAME | IL1, IM1, IH1 | | IL2, IM2, IH2 | | IL3, IM3, IH3 | |
|---|---|---|---|---|---|---|
| IMAGING DEVICE | ISX1 | ISY1 | ISX2 | ISY2 | ISX3 | ISY3 |
| LOW-PIXEL | 200 | 200 | 800 | 800 | 160 | 160 |
| MIDDLE-PIXEL | 400 | 400 | 1000 | 1000 | 160 | 160 |
| HIGH-PIXEL | 800 | 800 | 1000 | 1000 | 160 | 160 |

IMAGE PROCESSING APPARATUS TO GENERATE A REDUCED IMAGE OF AN ENDOSCOPIC IMAGE

BACKGROUND OF THE INVENTION

1. Field of the Invention

The present invention relates to an image processing apparatus configured to generate a reduced image of an endoscopic image.

2. Description of the Related Art

There are various types of the sizes of imaging devices (e.g., CCD, CMD, and CMOS) to be used in endoscopes. The sizes thereof are greatly different from each other depending, for example, on the differences among organs/parts to be observed, or the differences among the sizes/functions of endoscopes. When a narrow lumen, such as a bronchial tube or a biliary tract, is observed, an endoscope having a small diameter, in which an imaging device with a small number of pixels is mounted, is used. Additionally, in order to find a pathological change in an esophagus, stomach, large intestine, or the like, endoscopes of various sizes whose diameters range from a small one to a large one are used, and various imaging devices with pixels whose numbers range from a small one to a large one are mounted therein in accordance with the sizes. In an endoscope of a large size, there is generally room in the space of the tip portion thereof, and hence it is possible to mount an imaging device with a large number of pixels in which priority is placed on image quality.

When an organ/part to be observed is observed in detail, an endoscope, in which an imaging device with a large number of pixels is mounted, is used. On the other hand, when an organ/part is treated, or the like, an endoscope in accordance with the purpose of the treatment is used. In the former case, priority is placed on the capturing of an image with high quality and high resolution. In the latter case, priority is placed on the members for treatment, such as the diameter of a channel for making a treatment tool pass through, the number of the channels, or a water-jet function, and hence the size of an imaging device becomes relatively small. Thus, various imaging devices whose numbers of pixels and sizes are different from each other are used in endoscopes in accordance with design conditions based on the functions to be required.

Further, with the development of techniques, the number of pixels of an imaging device to be used in an endoscope is being increased. In the meantime, old model endoscopes are also usually designed to maintain compatibility with new system camera control units (CCUs: Camera Control Units) so as to be capable of being connected thereto. Although 20 years or more have passed since endoscopic images were videoized, three-generation old endoscopes can also be connected to new system CCUs. In such situations, when several-generation old endoscopes are compared with the latest ones, there are large differences between the numbers of pixels of imaging devices, in which the latest endoscopes have 10 to 20 times larger numbers of pixels.

An image captured by an endoscope is converted into an image for being displayed or recorded (hereinafter, appropriately referred to as an observation recorded image) by a CCU. An observation recorded image is typically generated by enlarging an image captured by an endoscope. Further, index images (they may be referred to as thumbnail images) are generated by reducing observation recorded images in order to be displayed in a list format. Each of the observation recorded image and the index image is typically generated to have a fixed size.

RELATED ART DOCUMENT

Patent Document

[Patent Document 1] Japanese Patent Application Publication No. 2012-5044

SUMMARY OF THE INVENTION

When an index image is generated by reducing an observation recorded image, aliasing may be caused. In order to suppress the aliasing, it is effective to perform band suppression processing on an observation recorded image to be reduced. If the band suppression is performed excessively, excessive smoothing is caused. Conversely, if the band suppression is performed insufficiently, aliasing cannot be fully removed. In particular, original images of endoscopic images, which are yet to be converted into observation recorded images, have various sizes, and hence the image quality of an index image is likely to be decreased by excessive smoothing or aliasing.

The present invention has been made in view of these situations, and a purpose of the invention is to provide a technique for reducing an observation recorded image so as to have high quality.

An image processing apparatus according to an embodiment of the present invention comprises: a filtering unit configured to apply a filter for suppressing a high-frequency component to a second image generated by performing image processing including at least enlargement processing on a first image captured by using an endoscope; an image reducing unit configured to generate a third image by performing reduction processing on the second image to which the filter has been applied; and a filter setting unit configured to set the characteristic of the filter based on both information on a maximum frequency component that can be reproduced in at least the first image and information on a maximum frequency component that should be reproduced in the third image.

Arbitrary combinations of the aforementioned constituting elements and implementations of the invention in the form of methods, apparatuses, systems, recording mediums, and computer programs and so forth may also be effective as additional modes of the present invention.

BRIEF DESCRIPTION OF THE DRAWINGS

Embodiments will now be described, byway of example only, with reference to the accompanying drawings, which are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Figure 1:
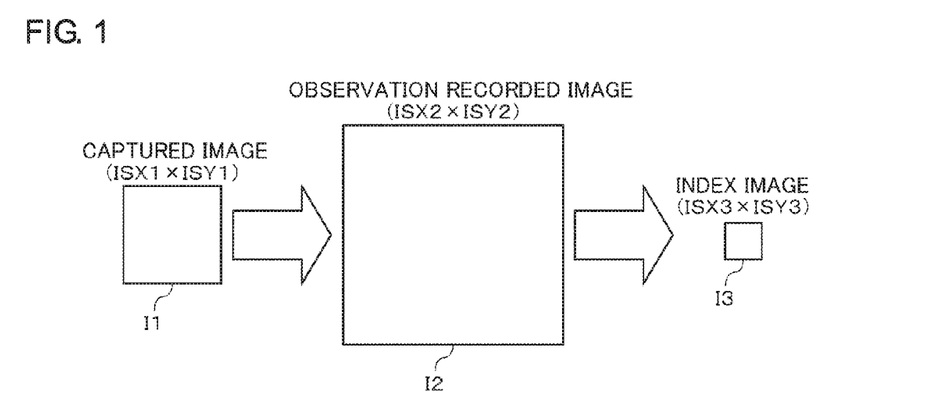
FIG. 1 is a view illustrating a relationship among a captured image, an observation recorded image, and an index image, which appear in the description according to the present embodiment.

Hereinafter, the basic principle of index image generation processing according to an embodiment of the present invention will be described. FIG. 1 is a view illustrating the relationship among a captured image I1, an observation recorded image I2, and an index image I3, which appear in the description according to the present embodiment. The size (ISX2×ISY2) of the observation recorded image I2 is usually larger than the size (ISX1×ISY1) of the captured image I1. That is, with the recent spread of HDTV (High Definition TeleVision) with high definition, a high-resolution screen size (1920×1080), etc., are being used even in endoscope systems. For the screen size, an endoscopic image having a size ISX2×ISY2 of 1000×1000 is displayed, for example, by performing enlargement processing on a captured image having a size ISX1×IS1 of 800×800. In the case of the conventionally spread SDTV (Standard Definition TeleVision), the ISX2×ISY2 is approximately 640×480 at maximum in most cases, and in such a case, the observation recorded image I2 may be generated by reducing the captured image I1. In this case, however, it can be considered that sufficient band suppression processing has already been performed on the image I2, and hence it is not necessary to take the size ISX1×ISY1 of the captured image I1 into consideration. When the observation recorded image I2 is generated from the captured image I1, image processing, such as gamma correction or color correction, is also executed before or after the enlargement processing. Thereby, the observation recorded image I2 that can be easily and visibly recognized is generated. When the observation recorded image I2 is generated, the captured image I1 is basically deleted.

There are various types in the size (ISX1×ISY1) of the captured image I1 due to the differences among the solid-state imaging devices included in endoscopes, but the types of the size (ISX2×ISY2) of the observation recorded image I2 is limited. This is done to allow doctors, etc., to observe the observation recorded images I2 having the same size as much as possible.

The size (ISX3×ISY3) of the index image I3 is mostly fixed, irrespective of the size (ISX1×ISY1) of the captured image I1 and the size (ISX2×ISY2) of the observation recorded image I2. Because the index images are mostly used for list display, a list display screen can be displayed neatly by unifying the sizes thereof.

Hereinafter, an example will be described, in which the index image I3 is generated from: a captured image IL1 with a small number of pixels (a low-pixel captured image IL1) captured by a low-pixel imaging device; a captured image IM1 with a middle number of pixels (a middle-pixel captured image IM1) captured by a middle-pixel imaging device; or a captured image IH1 with a large number of pixels (a high-pixel captured image IH1) captured by a high-pixel imaging device.

Figure 2:
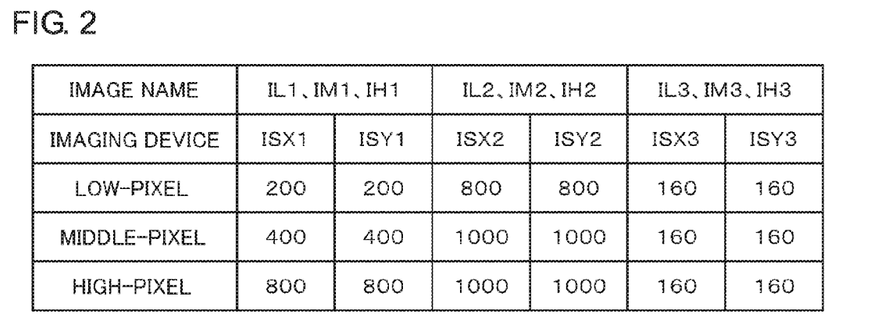
FIG. 2 is a table showing one example of the image size of: captured images captured by an imaging device with a small number of pixels (a low-pixel imaging device), an imaging device with a middle number of pixels (a middle-pixel imaging device) and an imaging device with a large number of pixels (a high-pixel imaging device), respectively; observation recorded images generated based on the captured images, respectively; and index images generated based on the observation recorded images, respectively.

FIG. 2 is a table showing one example of the image sizes of: the captured images IL1, IM1, and IH1 captured by a low-pixel imaging device, a middle-pixel imaging device, and a high-pixel imaging device, respectively; the observation recorded images IL2, IM2, and IH2 generated based on the captured images IL1, IM1, and IH1, respectively; and the index images IL3, IM3, and IH3 generated based on the observation recorded images IL2, IM2, and IH2, respectively. In the present specification, description will be made below assuming that the number of the effective pixels of an imaging device and the number of pixels of a captured image are the same as each other, for simplification.

More specifically, FIG. 2 shows one example of the image sizes of the images including: the low-pixel captured image IL1 captured by a low-pixel imaging device, the middle-pixel captured image IM1 captured by a middle-pixel imaging device, and the high-pixel captured image IH1 captured by a high-pixel imaging device; the low-pixel observation recorded image IL2 generated from the low-pixel captured image IL1, the middle-pixel observation recorded image IM2 generated from the middle-pixel captured image IM1, and the high-pixel observation recorded image IH2 generated from the high-pixel captured image IH1; and the low pixel index image IL3 generated from the low-pixel observation recorded image IL2, the middle-pixel index image IM3 generated from the middle-pixel observation recorded image IM2, and the high-pixel index image IH3 generated from the high-pixel observation recorded image IH2.

When an index image is generated by reducing an image, reduction processing is usually performed on the observation recorded image IL2, IM2, and IH2, not on the captured image IL1, IM1, and IH1. For the reduction processing, a common reduction algorithm, such as a simple thinning method, a bicubic method, or a linear interpolation method, can be used. When aliasing is caused by the reduction, band suppression processing is performed before the reduction processing is performed. For the band suppression processing, smoothing filtering or low-pass filtering is usually used.

In the simple band suppression processing, a maximum frequency is calculated based on the ratio of the number ISX2 of horizontal pixels/the number ISY2 of vertical pixels of the observation recorded image IL2 to the number ISX3 of horizontal pixels/the number ISY3 of vertical pixels of the index image I3, and then a filter having the effect of suppressing a frequency band component exceeding the maximum frequency is applied to the observation recorded image IL2. The maximum frequency corresponds to the concept of Nyquist frequency. For example, a maximum frequency fn2 in the high-pixel observation recorded image IH2, which is to be used when the high-pixel observation recorded image IH2 (image size is 1000×1000) is reduced to the high-pixel index image IH3 (image size is 160×160), is calculated by the following Equation (1):

$$fn2 = (160/1000) \times M \qquad \text{Equation (1)}.$$

Wherein, M is a numerical value corresponding to a maximum spatial frequency that can be reproduced in an image, and when it is assumed that, for example, 2M=256, M=128. It corresponds to the fact that, for example, maximum 128 pairs of white/black line pairs can be displayed on an image with an image size of 256, specifically, with 256 horizontal/vertical pixels. When M=128 is substituted in the above Equation (1), the maximum frequency fn2 becomes 20.4.

Figure 3:
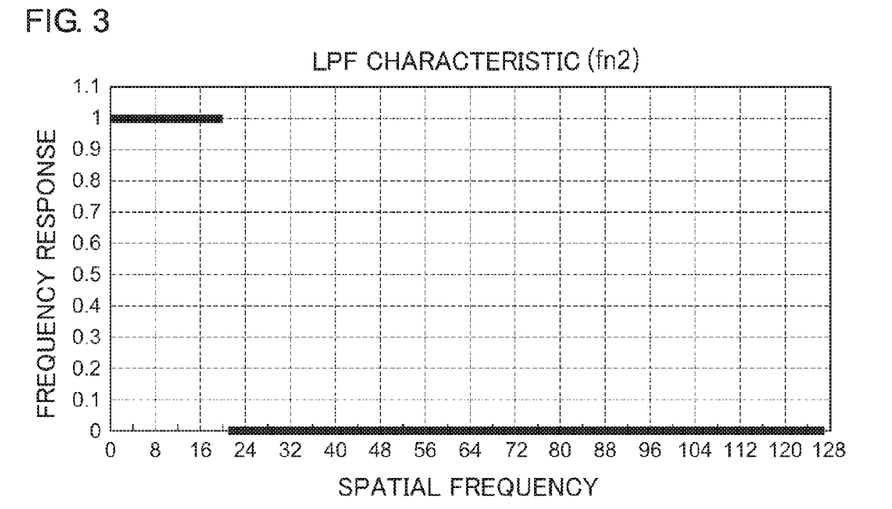
FIG. 3 is a graph showing the frequency response of a low-pass filter with an ideal characteristic.

FIG. 3 is a graph showing the frequency response of a low-pass filter with an ideal characteristic. The horizontal axis represents spatial frequencies, and the vertical axis represents frequency responses. This filter is one to be applied to the observation recorded image I2 as preprocessing for generating the index image I3. In the filter shown in FIG. 3, a frequency response becomes 1 when a spatial frequency is less than or equal to the maximum frequency fn2, while a frequency response becomes 0 when a spatial frequency is more than that. Alternatively, a filter provided with an approximate characteristic may be used, instead of a low-pass filter.

Although the band suppression has been theoretically described above, occurrence of aliasing is also dependent on what type of an object is actually imaged. In an endoscopic image for mainly observing the surface of a mucous membrane of a living body, a fine structure whose spatial frequency is close to the acceptable maximum frequency is rarely imaged in usual cases. However, aliasing is likely to be caused in some endoscopic images. For example, aliasing is likely to be caused in the edge portion of halation, because the portion exhibits a steep change. In special light observation, such as spraying of pigment or stain and NBI (Narrow Band Imaging), a relatively fine structure is imaged, and hence there is the high risk that aliasing may be caused. In view of these situations, it can be considered that a filter to be applied to the observation recorded image I2 is determined by designing a low-pass filter, etc., by which good image quality is obtained on average, and then by visually evaluating an effect on the index image I3.

However, the maximum frequency components present in the observation recorded image IL2, IM2, and IH3 are originally and basically defined by the number of pixels of an imaging device. Even if the sizes (ISX2×ISY2) of the observation recorded images IL2 are the same or almost the same as each other, the maximum frequency components, which can be present, respectively, in both the high-pixel observation recorded image IH2 generated based on the high-pixel captured image IH1 captured by a high-pixel imaging device and the low-pixel observation recorded image IL2 generated based on the low-pixel captured image IL1 captured by a low-pixel imaging device, are greatly different from each other.

If a band suppression filter produced for the high-pixel observation recorded image IH2 is applied to the low-pixel observation recorded image IL2, a smoothing effect is further added to an image in which fine structure components of a high-frequency band are originally few. Accordingly, blurring is caused in the index image IL3 generated by reducing the low-pixel observation recorded image IL2 to which the band suppression filter has been applied.

Conversely, if a band suppression filter, by which a reduced image with visually good image quality can be obtained from the low-pixel observation recorded image IL2 or the middle-pixel observation recorded image IM2, is applied to the high-pixel observation recorded image IH2, a sufficient band suppression effect cannot be obtained. That is, aliasing may be caused in the index image IH3 generated by reducing the high-pixel observation recorded image IH2 to which the band suppression filter has been applied.

In view of the facts described above, the frequency characteristic of a band suppression filter will be changed by taking the maximum frequency defined by the number of pixels of an imaging device into consideration in an embodiment of the present invention. Thereby, proper reduction processing can be performed on an image captured by any one of imaging devices with various numbers of pixels, whereby a reduced image with good image quality can be obtained. When a digital filter is used, the frequency characteristic of a band suppression filter is changed by changing the coefficient of the digital filter. When achieved by a combination of a plurality of filters, the frequency characteristic of a band suppression filter is changed by changing a manner in which the plurality of filters are combined, and/or by changing the number of times of repeated applications.

The maximum frequency to be used when the high-pixel observation recorded image IH2 is reduced will be first described. When the high-pixel index image IH3 is generated from the high-pixel captured image IH1, attention is paid to the size (ISX1×ISY1) of the high-pixel captured image IH1 and the size (ISX3×ISY3) of the high-pixel index image IH3. FIG. 2 shows an example in which the number ISX1 of horizontal pixels and the number ISY1 of vertical pixels of the high-pixel captured image IL11 are equal to each other, and the number ISX3 of horizontal pixels and the number ISY3 of vertical pixels of the high-pixel index image IH3 are equal to each other.

When the number of horizontal pixels is different from that of vertical pixels, the number of pixels are selected such that, for example, occurrence of aliasing may be avoided as much as possible. Specifically, the larger number of the number ISX1 of horizontal pixels and the number ISY1 of vertical pixels of the high-pixel captured image IL1 and the smaller number of the number ISX3 of horizontal pixels and the number ISY3 of vertical pixels of the high-pixel index image IH3 are selected. Alternatively, resolution may be taken into consideration, instead of the number of pixels. A maximum frequency fn1 in the captured image I1 is calculated by the following Equation (2):

$$fn1 = (ISX3/ISX1) \times M \qquad \text{Equation (2):}$$

When a high-pixel imaging device is used, the maximum frequency fn1 is calculated to be 25.6 by (160/800)×128.

Similarly, when a middle-pixel imaging device is used, the maximum frequency fn1 becomes 34.1, and when a low-pixel imaging device is used, it becomes 51.2.

Because actual band suppression processing (i.e., filtering processing) is performed on the observation recorded image I2, the size (ISX2×ISY2) of the observation recorded image I2 is taken into consideration for determining the frequency characteristic of a filter. A scale-converted maximum frequency fns is actually used. The scale-converted maximum frequency fns is calculate by the following Equation (3):

$$fns = ((ISX3/ISX1) \times M) \times (ISX2/ISX1) \quad \text{Equation (3).}$$

When a high-pixel imaging device is used, the scale-converted maximum frequency fns becomes 32. Similarly, when a middle-pixel imaging device is used, the maximum frequency fns becomes 56.8, and when a low-pixel imaging device is used, it becomes 82.4. Because a wavelength corresponding to one cycle of a frequency becomes large due to the enlargement from the captured image I1 to the observation recorded image I2, the scale-converted maximum frequency is changed toward a low frequency.

Figure 4:
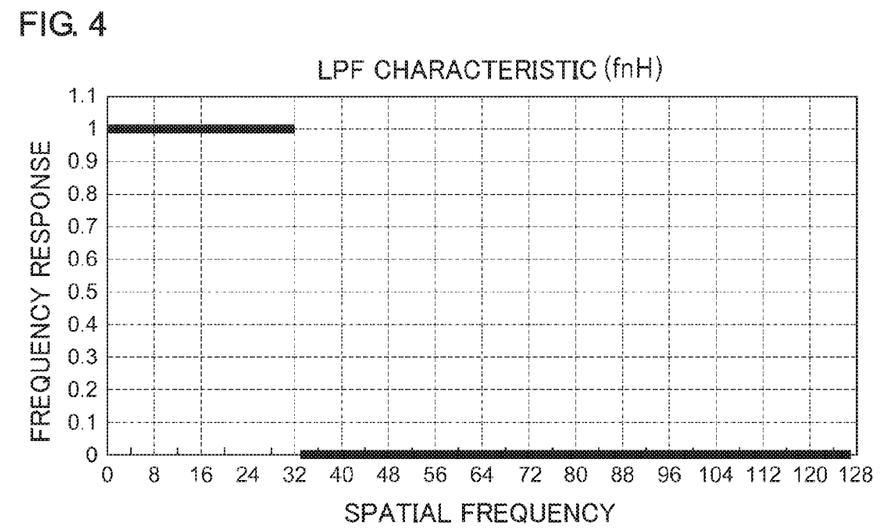
FIG. 4 is a graph showing the frequency response of a low-pass filter to be applied to an observation recorded image with a large number of pixels (a high-pixel observation recorded image)
Figure 5:
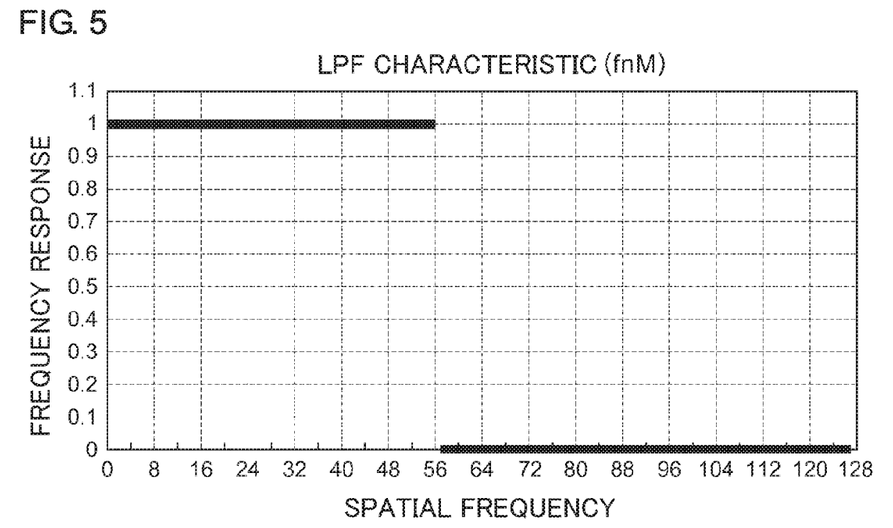
FIG. 5 is a graph showing the frequency response of a low-pass filter to be applied to an observation recorded image with a middle number of pixels (a middle-pixel observation recorded image)
Figure 6:
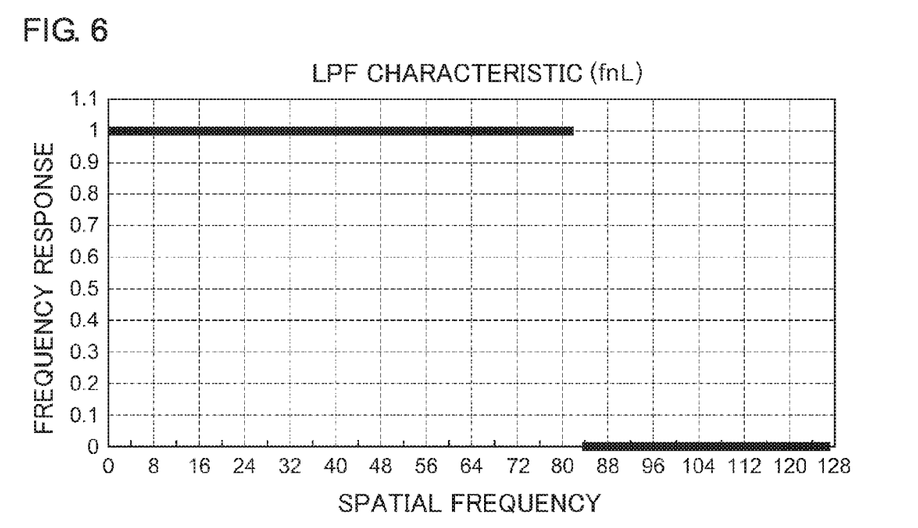
FIG. 6 is a graph showing the frequency response of a low-pass filter to be applied to an observation recorded image with a small number of pixels (a low-pixel observation recorded image)

FIG. 4 is a graph showing the frequency response of a low-pass filter to be applied to the high-pixel observation recorded image IH2. FIG. 5 is a graph showing the frequency response of a low-pass filter to be applied to the middle-pixel observation recorded image IM2. FIG. 6 is a graph showing the frequency response of a low-pass filter to be applied to the low-pixel observation recorded image IL2. Each of FIGS. 4 to 6 depicts a low-pass filter with an ideal characteristic. Although each of FIGS. 4 to 6 shows the frequency characteristic of a low-pass filter with an ideal characteristic, it is actually difficult to achieve the equivalent characteristic in an actual filter size. Accordingly, occurrence of excessive blurring is suppressed by performing band suppression→reduction→sharpness correction. Hereinafter, the maximum frequencies in the high-pixel observation recorded image IH2, the middle-pixel observation recorded image IM2, and the low-pixel observation recorded image IL2 are set to fnH=32, fnM=57, and fnL=83, respectively. These numeral values are obtained by rounding up digits after the decimal point of the aforementioned maximum frequencies.

Hereinafter, a method of achieving the aforementioned band suppression processing by filtering using a digital filter (more specifically, a convolution operation) will be described. In the following example, desired band suppression is achieved at high speed by a combination of filters with small sizes. Specifically, it is achieved by a combination of n×n (n: an integer of 3 or more (odd number)) Gaussian filters.

The following Equation (4) represents a Gaussian filter h3(k,l) with a mask size of 3×3 in which a Gaussian coefficient is used. The following Equation (5) represents a Gaussian filter h5(k,l) with a mask size of 5×5. The following Equation (6) represents a Gaussian filter h7(k,l) with a mask size of 7×7. A Gaussian filter is a filter in which, when a product-sum operation is performed, a weight for the luminance value of a pixel closer to a target pixel is made larger, unlike a moving average filter in which the luminance values of pixels around a target pixel are simply averaged. Each coefficient is determined by using a Gaussian distribution function. A Gaussian filter has an operation similar to that of a low-pass filter.

$$h3(k, l) = \begin{cases} 0.0682850 & 0.1125830 & 0.682850 \\ 0.1125830 & 0.2765270 & 0.1125830 \\ 0.682850 & 0.1125830 & 0.0682850 \end{cases} \quad \text{EQUATION 4}$$

$$h5(k, l) = \begin{cases} 0.0682850 & 0 & 0.1125830 & 0 & 0.0682850 \\ 0 & 0 & 0 & 0 & 0 \\ 0.1125830 & 0 & 0.2765270 & 0 & 0.1125830 \\ 0 & 0 & 0 & 0 & 0 \\ 0.0682850 & 0 & 0.1125830 & 0 & 0.0682850 \end{cases} \quad \text{EQUATION 5}$$

$$h7(k, l) = \begin{cases} 0.0682850 & 0 & 0 & 0.1125830 & 0 & 0 & 0.0682850 \\ 0 & 0 & 0 & 0 & 0 & 0 & 0 \\ 0 & 0 & 0 & 0 & 0 & 0 & 0 \\ 0.1125830 & 0 & 0 & 0.2765270 & 0 & 0 & 0.1125830 \\ 0 & 0 & 0 & 0 & 0 & 0 & 0 \\ 0 & 0 & 0 & 0 & 0 & 0 & 0 \\ 0.0682850 & 0 & 0 & 0.1125830 & 0 & 0 & 0.0682850 \end{cases} \quad \text{EQUATION 6}$$

The 5×5 Gaussian filter h5(k,l) represented by Equation (5) and the 7×7 Gaussian filter h7(k,l) represented by Equation (6) are generated by interpolating 0 into the 3×3 Gaussian filter h3(k,l). Thereby, the number of times of multiplication can be suppressed to 9, similarly to the 3×3 Gaussian filter h3(k,l), whereby a high-speed operation can be performed.

Figure 7:
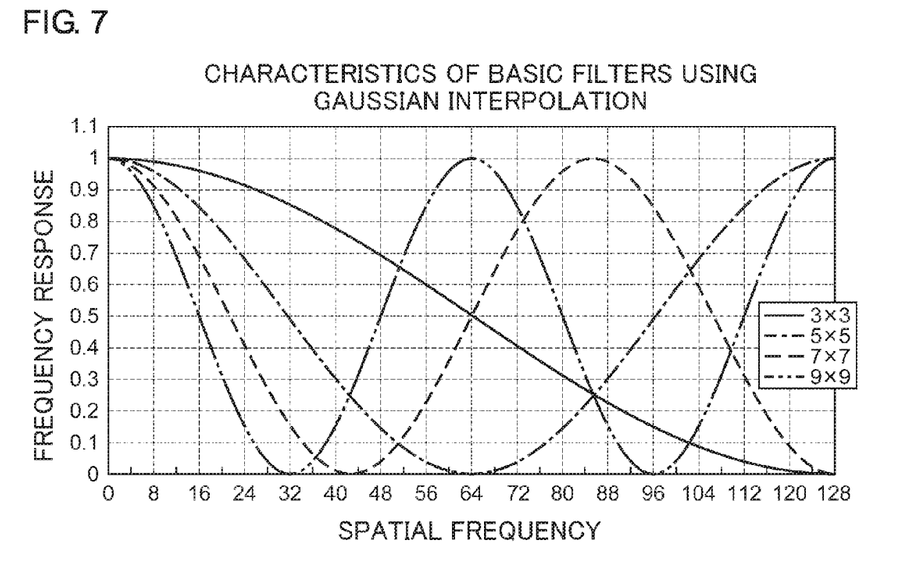
FIG. 7 is a graph showing the frequency responses of Gaussian filters.

FIG. 7 is a graph showing the frequency responses of Gaussian filters. FIG. 7 shows the frequency responses of the 3×3 Gaussian filter h3(k,l) represented by Equation (4), the 5×5 Gaussian filter h5(k,l) represented by Equation (5), the 7×7 Gaussian filter h7(k,l) represented by Equation (6), and a 9×9 Gaussian filter h9(k,l). The 9×9 Gaussian filter h9(k,l) is also generated by interpolating 0 into the 3×3 Gaussian filter h3(k,l).

Various frequency characteristics can be achieved by combining these basic Gaussian filters. That is, various frequency characteristics can be achieved by performing a convolution operation with an arbitrary combination of these Gaussian filters. Alternatively, the same Gaussian filter may be used multiple times.

Figure 8:
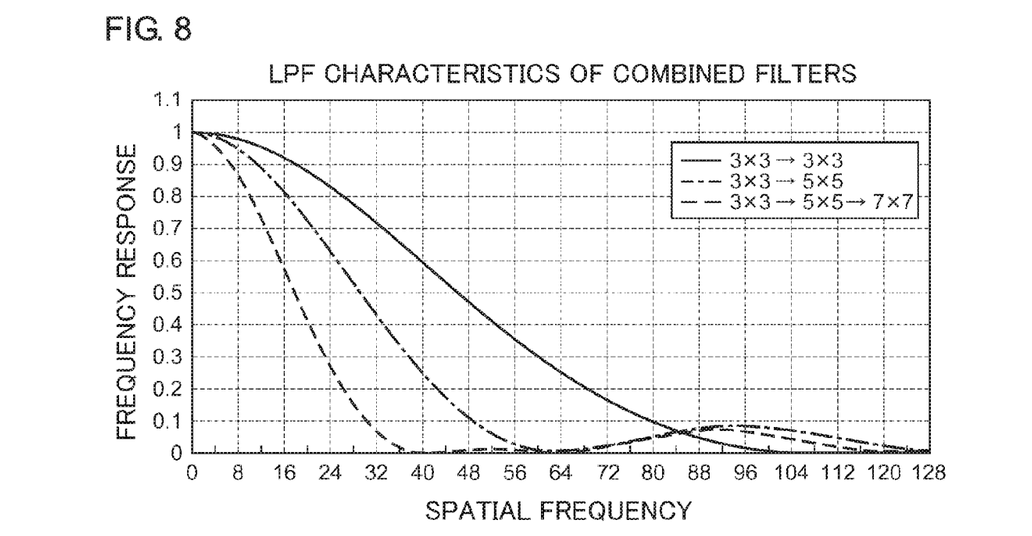
FIG. 8 is a graph showing the frequency responses of filters formed by combining the Gaussian filters in FIG. 7.

FIG. 8 is a graph showing the frequency responses of filters formed by combining the Gaussian filters in FIG. 7. FIG. 8 shows the frequency responses of a filter of h3(k,l)*h3(k,l), a filter of h3(k,l)*h5(k,l), and a filter of h3(k,l)*h5(k,l)*h7(k,l). Herein, * represents a convolution operation.

In the above example, the maximum frequency fnL in the low-pixel observation recorded image IL2 is set to 83. In the filter of h3(k,l)*h3(k,l), the frequency band component for a spatial frequency of 80 or more can be suppressed to 0.1 or less. Accordingly, a frequency band component exceeding the maximum frequency fnL can be suppressed by applying the 3×3 Gaussian filter h3(k,l) to the low-pixel observation recorded image IL2 and by applying again the 3×3 Gaussian filter h3(k,l) to the image having been subjected to the filtering. In the present embodiment, it is defined that the suppression of a frequency band component is achieved when a frequency response is less than 0.1.

In the aforementioned example, the maximum frequency fnM in the middle-pixel observation recorded image IM2 is set to 57. In the filter of h3(k,l)*h5(k,l), the frequency band component for a spatial frequency of 48 or more can be suppressed to 0.1 or less. Accordingly, a frequency band component exceeding the maximum frequency fnM can be suppressed by applying the 3×3 Gaussian filter h3(k,l) to the middle-pixel observation recorded image IM2 and then by applying the 5×5 Gaussian filter h5(k,l) to the image having been subjected to the filtering.

In the aforementioned example, the maximum frequency fnH in the high-pixel observation recorded image IH2 is set to 32. In the filter of h3(k,l)*h5(k,l)*h7(k,l), the frequency band component for a spatial frequency of 25 or more can be suppressed to 0.1 or less. Accordingly, the frequency band component exceeding the maximum frequency fnH can be suppressed by applying the 3×3 Gaussian filter h3(k,l) to the high-pixel observation recorded image IH2, and by applying the 5×5 Gaussian filter h5(k,l) to the image having been subjected to the filtering, and by applying the 7×7 Gaussian filter h7(k,l) to the image having been subjected to the filtering.

The good index image I3, in which aliasing is not caused, can be obtained by reducing the observation recorded image I2 having been subjected to the above filtering. For the reduction processing, a general technique, such as a bicubic method, can be used. A bicubic method also has a slight band suppression effect, and hence, taking it into consideration, the band suppression effect by the filtering before the reduction processing may be slightly weakened.

Further, sharpness correction using a sharpness correction filter may be performed on the generated index image I3. The sharpness correction filter has an amplification effect over the frequency band components remaining in the index image I3 without being subjected to band suppression, i.e., the frequency band components that have passed through the low-pass filter. The sharpness correction filter can be formed by a high-pass filter that makes a high-frequency component pass through. The following Equation (7) represents one example of a sharpness correction filter to be applied to the high-pixel index image IH3. This filter h3s(k,l) is a high-pass filter in an opposite relationship with the Gaussian filter h3(k,l) having the band suppression effect represented in the above Equation (4), and has the effect of extracting high-frequency band components (many of them are edge components) on an image.

$$h3s(k, l) = \begin{cases} -0.0682850 & -0.1125830 & -0.0682850 \\ -0.1125830 & 0.723473 & -0.1125830 \\ -0.0682850 & -0.1125830 & -0.0682850 \end{cases} \quad \text{EQUATION 7}$$

A high-frequency index image $gH3(x, y)$, to which the sharpness correction filter represented by the above Equation (7) has been applied, is generated by the following Equation (8):

$$gH3(x,y)=IH3(x,y)*h3s(k,l) \quad \text{Equation (8).}$$

The sharpness-corrected high-pixel index image $IH3'(x,y)$ is generated by correcting the high-pixel index image IH3 $(x,y)$ with the high-frequency index image $gH3(x,y)$. The sharpness-corrected high-pixel index image $IH3'(x,y)$ is generated by adding a weighted high-frequency index image $\lambda gH3(x,y)$ to the high-pixel index image $IH3(x,y)$, as represented by the following Equation (9):

$$IH3'(x,y)=IH3(x,y)+\lambda gH3(x,y) \quad \text{Equation (9).}$$

$\lambda$ is set, for example, to 0.2. A sharpness-corrected middle-pixel index image $IM3'(x,y)$ and a sharpness-corrected low-pixel index image $IL3'(x,y)$ can also be generated in a similar manner.

By changing the frequency characteristic of a band suppression filter, taking a maximum frequency defined by the number of pixels of an imaging device into consideration, proper reduction processing can be performed on an image captured by any one of imaging devices with various numbers of pixels, as described above, thereby allowing a reduced image with good image quality to be obtained.

(First Variation)

Subsequently, a method of performing, with saved resources and at high speed, the aforementioned filtering processing for band suppression will be described. As described above, the high-pixel index image $IH3(x,y)$ is generated by convolving the aforementioned a plurality of Gaussian filters in the high-pixel observation recorded image $IH2(x,y)$, as represented by the following Equation (10):

$$IH3(x,y)=((IH2(x,y)*h3(k,l))*h5(k,l))*h7(k,l) \quad \text{Equation (10).}$$

In the filtering processing on the right-hand side, the image size of the high-pixel observation recorded image IH2 is always ISX2×ISY2.

Herein, a frequency band component of approximately 64 (=M/2) or more is already and sufficiently suppressed in the frequency characteristic obtained when the 3×3 Gaussian filter h3(k,l) and the 5×5 Gaussian filter h5(k,l) are combined together. The following Equation (11) represents a middle image $IH2b(x,y)$ obtained when the filtering using the 5×5 Gaussian filter h5(k,l) represented by the above Equation (10) is completed.

$$IH2b(x,y)=(IH2(x,y)*h3(k,l))*h5(k,l) \quad \text{Equation (11).}$$

Even if the size of the middle image $IH2b(x,y)$ is reduced to ½, aliasing is not caused.

A memory area can be reducible by this reduction processing. Further, the calculation amount of the filtering can be reduced, and hence the filtering processing can be performed at high speed. Another band suppression filter ht(k, l), not the 7×7 Gaussian filter h7(k,l) in the above Equation (10), is applied to the middle image $IH2b'$ reduced to ½ by a bicubic method, or the like. The high-pixel index image $IH3(x,y)$ can also be obtained by this.

For the band suppression filter ht(k,l), a filter with a frequency characteristic gentler than the 7×7 Gaussian filter h7(k,l) is used. Because the middle image IH2b is reduced to ½, 3.5×3.5 Gaussian filter h3.5(k,l) should be used ideally, but it is difficult to achieve. So, the 3×3 Gaussian filter (k,l) or the 5×5 Gaussian filter h5(k,l) is used. When the 5×5 Gaussian filter h5(k,l) is applied, a slightly stronger band suppression effect is exhibited in comparison with the filtering processing represented by the above Equation (10), but it can be corrected by causing $\lambda$ in the sharpness correction processing of the above Equation (9) to be larger.

Although an example, in which the size of the middle image $IH2b(x,y)$ is reduced to ½, has been described in the aforementioned example, it is also possible to reduce the size to a level other than ½. For example, when a frequency band component of approximately 86 (=2M/3) or more is sufficiently suppressed in the middle image $IH2b(x,y)$ yet to be reduced, the size of the middle image $IH2b(x,y)$ can be reduced to ⅔. In this case, the size of the Gaussian filter to be applied thereafter can be reduced to ⅔.

As described above, an operation amount can be reduced by reducing an image in the middle of a convolution operation with a plurality of Gaussian filters, thereby allowing a high-speed operation to be performed with saved resources.

(Second Variation)

Subsequently, an example will be described, in which, when a maximum frequency fn in each of the captured image I1 and the observation recorded image I2 is calculated, optical design other than the number of pixels of an imaging device, and MTF (Modulation Transfer Function)

of the whole system are taken into consideration. In an actual endoscope system, the maximum frequency fn in each of the captured image I1 and the observation recorded image I2 is affected by the following factors other than the number of pixels of an imaging device.

As a factor affecting the maximum frequency fn, there is optical design including a lens in an endoscope. The maximum resolution and the width of a depth of field of an imaging device are generally in a trade-off relationship. For example, if design is performed by placing priority on a depth of field, a high-frequency component corresponding to the maximum resolution of an imaging device is not generated. The design, in which priority is placed on a depth of field, means the design for allowing a wide range to be observed in accordance with the distance with a target. That is, it means the design in which a depth of field is large.

Various image processing are mainly performed inside a CCU. Some of those image processing, such as noise suppression processing and enhancement processing, may affect MTF of the whole system comprising an endoscope and a CCU. Or, electrical signal degradation may be caused. These also become factors affecting the maximum frequency fn.

Figure 9:
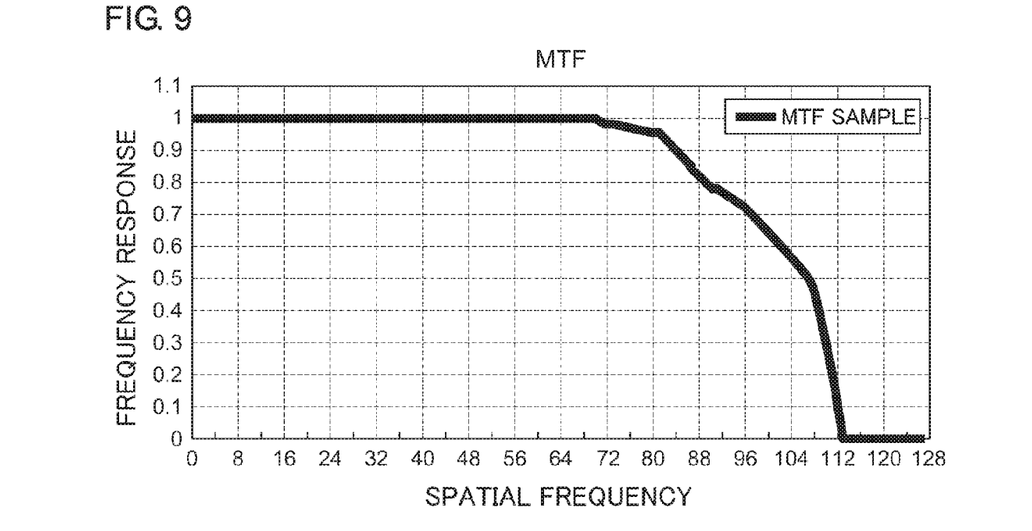
FIG. 9 is a graph showing an example of the frequency response of MTF of the whole system comprising an endoscope and a CCU, when an observation recorded image is generated.

FIG. 9 is a graph showing one example of the frequency response of MTF of the whole system comprising an endoscope and a CCU, when the observation recorded image I2 is generated. In this example, the frequency response becomes o, when the spatial frequency is 112. Even if a high-pixel imaging device, for example, with the number ISX1 of horizontal pixels of 800 and the number ISY1 of vertical pixels of 800 is used, a substantial maximum frequency component becomes 800×(112/128)=700. That is, it becomes similar to the maximum frequency component of an imaging device with the number ISX1 of horizontal pixels of 700 and the number ISY1 of vertical pixels of 700.

Hereinafter, processing for generating the high-pixel index image IH3, in which these factors are taken into consideration, will be described. The respective image sizes of the high-pixel captured image IH1, the high-pixel observation recorded image IH2, and the high-pixel index image IH3 are the same as those in the above FIG. 2. When a numerical value, in which MTF of the whole system is taken into consideration, is substituted in the right-hand side of Equation (3), the term becomes (160/(800×(112/128))× 128)×(1000/(800×(112/118))). When the term is solved, the scale-converted maximum frequency fns in the high-pixel observation recorded image IH2 becomes 41.8.

Figure 10:
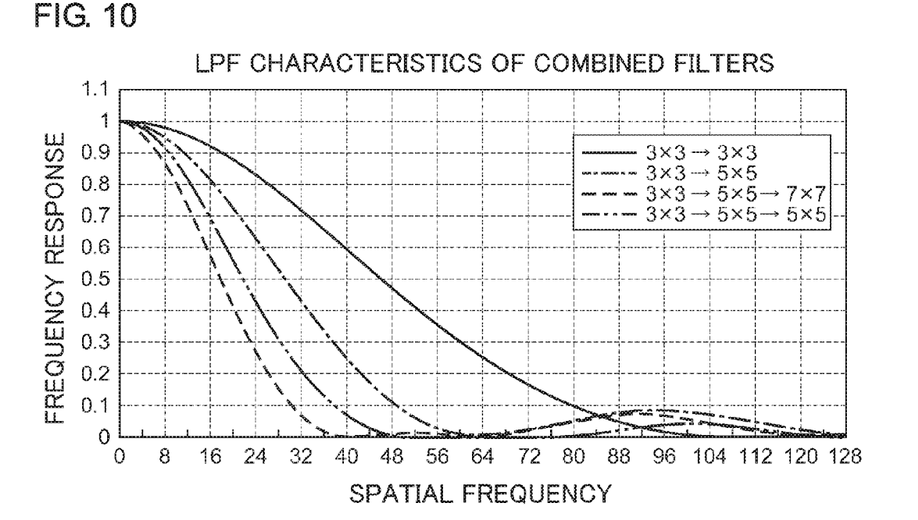
FIG. 10 is a view in which the frequency responses of a filter h3(k,l)*h5(k,l)*h5(k,l) is added to FIG. 8 (* represents a convolution operation)

FIG. 10 is a view in which the frequency responses of a filter h3(k,l)*h5(k,l)*h5(k,l) is added to FIG. 8. When the maximum frequency fns=41.8, it is proper to use the filter h3(k,l)*h5(k,l)*h5(k,l), not the filter h3(k,l)*h5(k,l)*h7(K,l).

Thus, band suppression processing, in which the optical and electrical MTF of the whole system is taken into consideration, may be performed, in addition to the maximum frequency based on the number of pixels (in other words, the maximum resolution) of an imaging device. For example, when MTF of a system is changed depending on the models of endoscopes different from each other in optical design or on the setting states of a CCU, a reduced image with flexible and good image quality can be generated by performing proper band suppression processing for every model and setting state thereof.

In the transition region of a frequency characteristic where a frequency response is less than 1, degradation (i.e., attenuation) of a frequency component is caused; however, this can be corrected by the sharpness correction processing described by using the above Equations (8) and (9).

Figure 11:
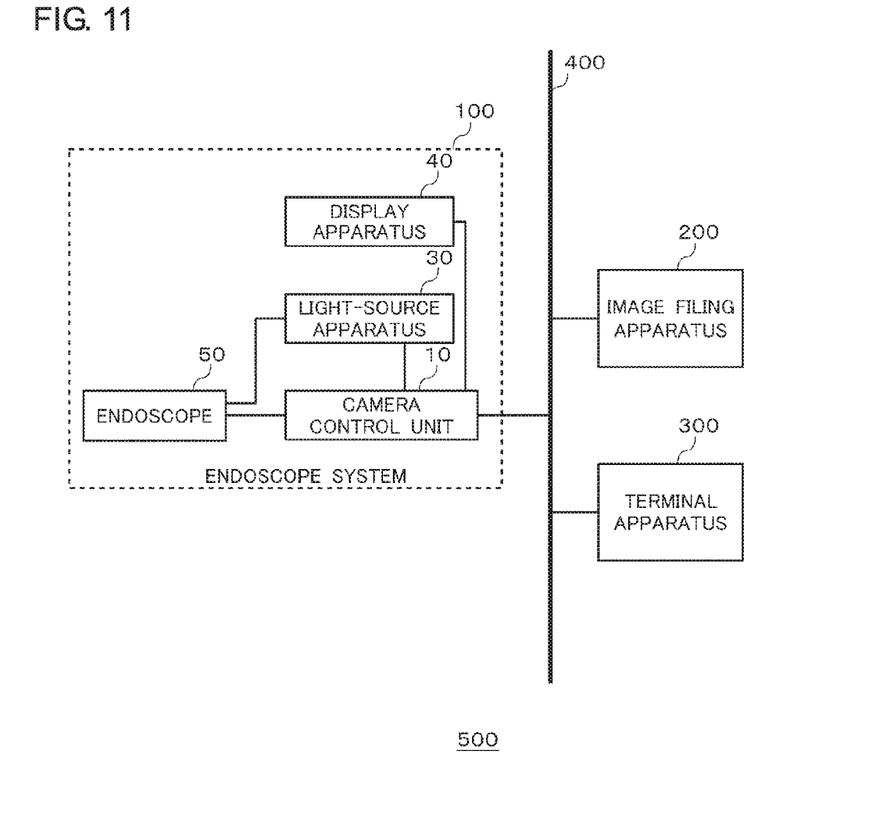
FIG. 11 is a view illustrating a configuration of a medical image management system according to an embodiment of the present invention.

Hereinafter, a medical image management system, in which an index image generating function based on the aforementioned knowledge is implemented, will be described. FIG. 11 is a view illustrating a configuration of a medical image management system 500 according to an embodiment of the present invention. The medical image management system 500 according to the present embodiment is a system for managing the images mainly captured by an endoscope 50. The medical image management system 500 comprises an endoscope system 100, an image filing apparatus 200, and a terminal apparatus 300, which are connected to each other via a communication line 400. The communication line 400 is assumed to be a wired LAN in the present embodiment. Although FIG. 11 illustrates only one endoscope system 100, a plurality of the endoscope systems 100 may be connected to the communication line 400. A plurality of the endoscope systems 100 are generally installed in a large hospital.

The endoscope system 100 includes a camera control unit 10, a light-source apparatus 30, a display apparatus 40, and the endoscope 50. The endoscope 50 is used by being inserted into the body cavity of a patient. The endoscope 50 images the inside of the body cavity and outputs it to the camera control unit 10.

There are various types of the endoscopes 50. Specifically, there are different scopes for different parts of a body, including scopes for: an upper gastrointestinal tract, a lower gastrointestinal tract, a duodenum, a bronchial tube, and the like. Those scopes are further subdivided according to their use or features. For example, upper gastrointestinal tract scopes include a general-purpose scope, a narrow-diameter scope, a pernasal scope, an optical magnification scope, a scope for treatment, and the like. There are also ultrasonic scopes that use ultrasonic waves. There are also capsule-shaped capsule endoscopes.

The camera control unit 10 receives an image signal transmitted from the endoscope 50, and processes the image signal. The specific configuration and operation of the camera control unit 10 will be described later. The light-source apparatus 30 sends light into the endoscope 50. The display apparatus 40 displays an image based on a video signal input from the camera control unit 10. The display apparatus 40 displays, for example, the image currently being captured by the endoscope 50 in real time. Although not illustrated in FIG. 11, the endoscope system 100 may include a printer or a recorder.

Figure 12:
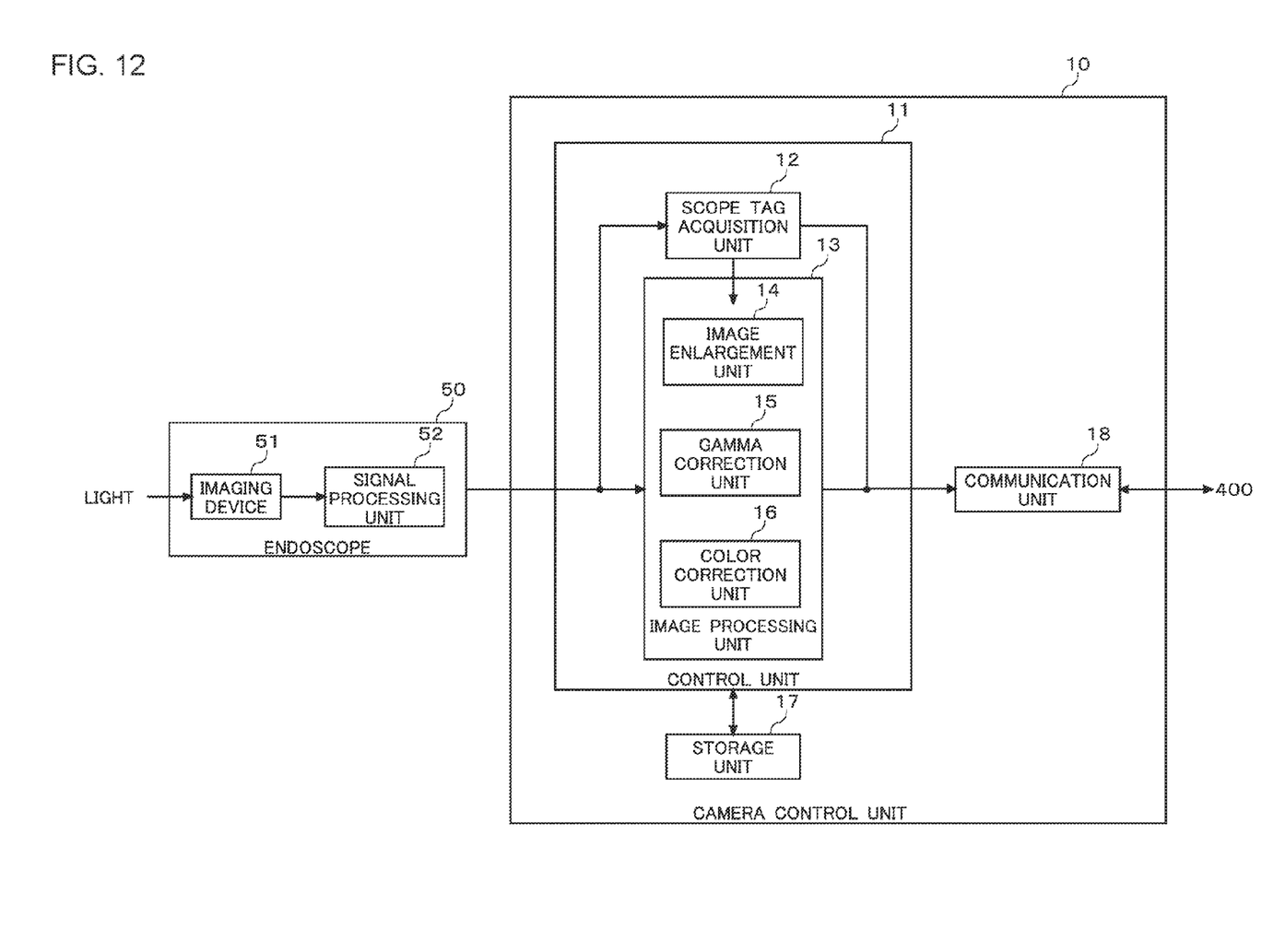
FIG. 12 is a view illustrating internal configurations of the endoscope 50 and the CCU in FIG. 11.

FIG. 12 is a view illustrating internal configurations of the endoscope 50 and the camera control unit 10 in FIG. 11. The endoscope 50 includes an imaging device 51 and a signal processing unit 52. The imaging device 51 converts incident light into an electrical signal. The signal processing unit 52 performs signal processing, such as A/D conversion or noise removal, on the image signal photoelectric-converted by the imaging device 51, and outputs it to the camera control unit 10.

The camera control unit 10 includes a control unit 11, a storage unit 17, and a communication unit 18. The control unit 11 includes a scope tag acquisition unit 12 and an image processing unit 13. In the functional blocks in the control unit 11, functions relevant to the aforementioned index image generating function are only illustrated. The functions of the control unit 11 are achieved by only hardware resources or by coordination of hardware resources and software resources. CPUs, FPGAs (Field Programmable Gate Arrays), and other LSIs can be used as the hardware resources. The programs readout from the storage unit 17 can be used as the software resources. The storage unit 17 includes a ROM and a RAM in order to store the programs and data to be used by the control unit 11.

The scope tag acquisition unit 12 acquires tag information from the endoscope 50, when the endoscope 50 is installed in the camera control unit 10. In the index image generation method according to the present embodiment, the number of pixels of an imaging device is used, as described above. When the tag information includes the numbers of horizontal and vertical effective pixels of the imaging device 51, the numbers thereof can be used.

In the design in which the tag information that can be acquired from the endoscope 50 does not include the number of pixels of the imaging device 51, it is necessary to provide, in advance, a table in which a model number included in the tag information and the number of pixels of an imaging device to be used in an endoscope with the model number are linked together. Alternatively, when a captured image captured by the imaging device 51 records, as tag information, the numbers of horizontal and vertical pixels of the captured image, the numbers thereof can be used. The scope tag acquisition unit 12 presents the number of pixels of the imaging device 51 to the image processing unit 13.

The image processing unit 13 performs image processing including at least enlargement processing on a captured image captured by using the endoscope 50. In the example illustrated in FIG. 12, the image processing unit 13 includes an image enlargement unit 14, a gamma correction unit 15, and a color correction unit 16.

The image enlargement unit 14 enlarges the captured image transmitted from the endoscope 50 such that an observation recorded image is generated. In that case, an enlargement ratio is set in accordance with the ratio of the number of pixels of the imaging device 51 presented from the scope tag acquisition unit 12 to the number of pixels of an observation recorded image to be generated.

The gamma correction unit 15 performs gamma correction on the generated observation recorded image. The color correction unit 16 performs color correction on the generated observation recorded image. The color correction unit 16 may perform correction in which, for example, redness is enhanced. Herein, the gamma correction and the color correction are examples of image processing, and other effect processing may be performed. For example, brightness adjustment, contour enhancement, contrast adjustment, or the like, may be performed. These image processing may be performed on a captured image before enlargement processing. When an observation recorded image is generated, a captured image basically becomes unnecessary, whereby it is discarded.

The communication unit 18 performs communication control such that the camera control unit 10 is connected to the communication line 400. The control unit 11 transmits the generated observation recorded image to the image filing apparatus 200 via the communication line 400 so as to be filed. The control unit 11 also transmits the number of pixels of the imaging device 51 to the image filing apparatus 200 via the communication line 400.

Figure 13:
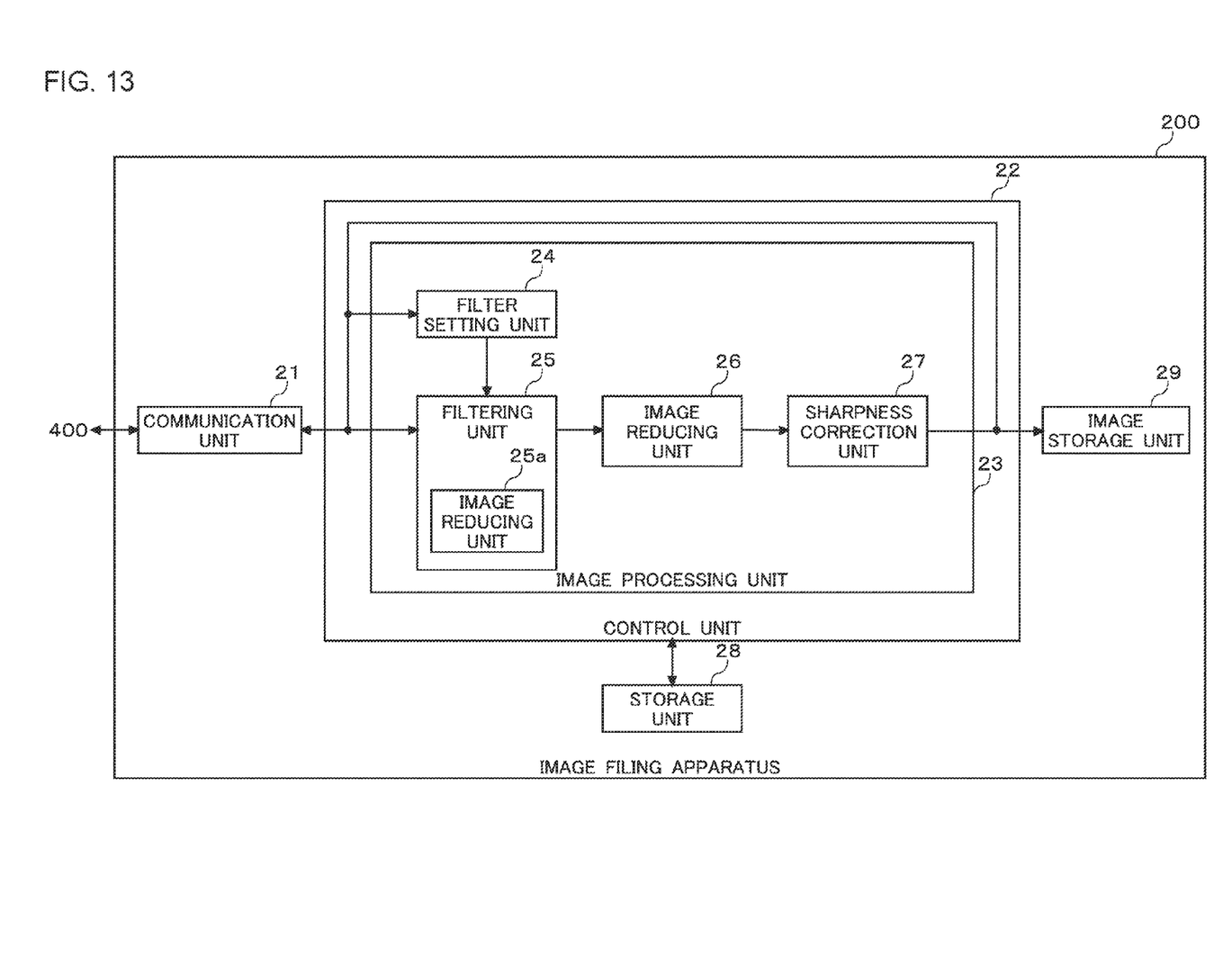
FIG. 13 is a view illustrating an internal configuration of the image filing apparatus in FIG. 11.

FIG. 13 is a view illustrating an internal configuration of the image filing apparatus 200 in FIG. 11. The image filing apparatus 200 is formed, for example, by a server. The image filing apparatus 200 includes a communication unit 21, a control unit 22, a storage unit 28, and an image storage unit 29.

The communication unit 21 performs communication control such that the image filing apparatus 200 is connected to the communication line 400. The communication unit 21 receives, for example, the number of pixels of the observation recorded image and that of the imaging device 51, which have been transmitted from the endoscope system 100, and outputs them to the control unit 22. The communication unit 21 also transmits the observation recorded image and/or the index image, read out by the control unit 22 from the image storage unit 29, to the terminal apparatus 300 in response to an acquisition request from the terminal apparatus 300. The image storage unit 29 includes a large-capacity recorder, such as a hard disk, and stores medical images including observation recorded images. When an index image of a medical image is generated, the image storage unit 29 also stores the index image.

The control unit 22 includes an image processing unit 23. In the functional blocks in the control unit 22, functions relevant to the aforementioned index image generating function are only illustrated. The functions of the control unit 22 are achieved by only hardware resources or by coordination of hardware resources and software resources. CPUs, FPGAs, and other LSIs can be used as the hardware resources. The programs read out from the storage unit 28 can be used as the software resources. The storage unit 28 includes a ROM and a RAM in order to store the programs and data to be used by the control unit 22.

The image processing unit 23 includes a filter setting unit 24, a filtering unit 25, an image reducing unit 26, and a sharpness correction unit 27. The filtering unit 25 applies a filter for suppressing a high-frequency component to the observation recorded image received from the endoscope system 100. For the filter, the aforementioned low-pass filter is used. The image reducing unit 26 performs reduction processing on the observation recorded image to which the low-pass filter has been applied, whereby an index image is generated. The sharpness correction unit 27 performs sharpness correction processing using the aforementioned sharpness correction filter on the generated index image.

The filter setting unit 24 changes the characteristics of the low-pass filter to be used by the filtering unit 25 based on the information on a maximum frequency component that can be reproduced in at least a captured image and the information on a maximum frequency component that should be reproduced in an index image. The information on a maximum frequency component that can be reproduced in the captured image may be information based on the number of pixels of the imaging device 51 included in the endoscope 50. The information on a maximum frequency component that should be reproduced in an index image may be information based on the number of pixels of the index image.

In this case, the filter setting unit 24 changes the characteristics of the low-pass filter based on the ratio of the number of horizontal/vertical pixels of a captured image to the number of horizontal/vertical pixels of an index image. More specifically, the filter setting unit 24 derives a maximum frequency at which aliasing is not caused in an index image based on: (1) the ratio of the number of horizontal/vertical pixels of a captured image to the number of horizontal/vertical pixels of the index image; (2) the maximum spatial frequency of an image; and (3) the number of horizontal/vertical pixels of the captured image to the number of horizontal/vertical pixels of an observation recorded image. This maximum frequency corresponds to the scale-converted maximum frequency fns represented by the Equation (3). When the maximum frequency is derived, MTF of the whole system comprising the endoscope 50 and the camera control unit 10 may be added.

The filter setting unit 24 sets the aforementioned low-pass filter so as to suppress a frequency component exceeding the maximum frequency. As illustrated in FIG. 8, the low-pass filter can be achieved by a combination of basic Gaussian filters. In this case, the filter setting unit 24 performs a plurality of filter operations (in other words, convolution operations) on an observation recorded image.

The filtering unit 25 includes an image reducing unit 25a, and the image reducing unit 25a may reduce an observation recorded image, on which at least one filter operation has been performed, with a reduction ratio within a range where aliasing is not caused, in the middle of the plurality of filter operations. By reducing a middle-image in the middle of the plurality of filter operations, as described above, the operation amount of a subsequent filter operation can be reduced.

Setting information on: the selection of a frequency characteristic for band suppression to the maximum frequency; the combination of basic filters; the reduction processing to be performed in the middle of band suppression processing; and the sharpness correction processing, which have been described above, can be written, in advance, in software programs by a designer. There are many types of the endoscope 50 to be installed in the camera control unit 10, but the number of the types of the imaging device 51 is some extent, for example, 10 or so. The number of the types of the sizes of each of an observation recorded image and an index image is one to several. Accordingly, the types of the aforementioned maximum frequency are not so many, and it is relatively easy to specify, in advance, filtering strategies for all the types of the maximum frequency. Alternatively, a structure may be adopted, in which a filtering strategy for each maximum frequency is written in a table, not in a software program, so that a software program can refer to.

The terminal apparatus 300 in FIG. 11 is formed, for example, by a personal computer (PC). The terminal apparatus 300 is mainly used for inputting reports or checking captured medical images by a doctor. The terminal apparatus 300 can acquire the index images of the observation recorded images recorded in the image filing apparatus 200, and display them in a list format.

Figure 14:
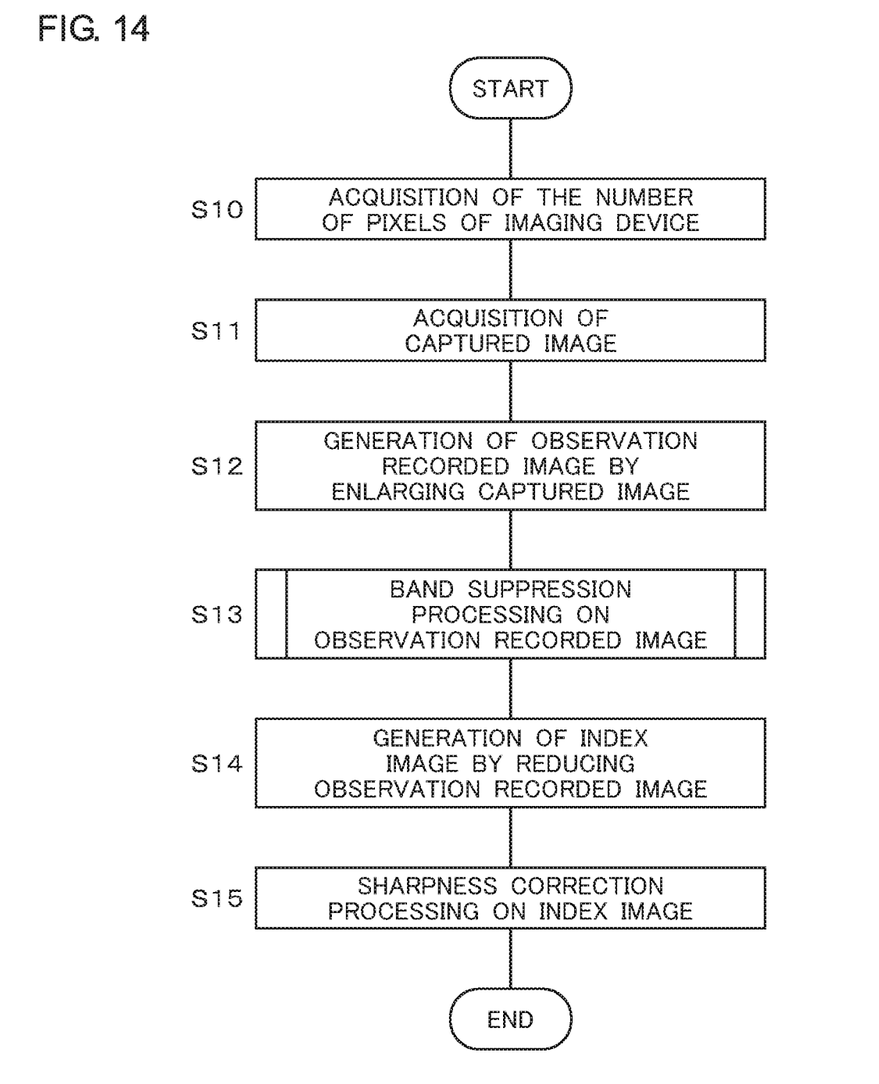
FIG. 14 is a flowchart illustrating an index image generation method according to an embodiment of the invention.

FIG. 14 is a flowchart illustrating an index image generation method according to an embodiment of the present invention. The scope tag acquisition unit 12 in the camera control unit 10 acquires the number of pixels of the imaging device 51 from the endoscope 50 (S10). The image processing unit 13 in the camera control unit 10 acquires an captured image captured by the imaging device 51 from the endoscope 50 (S11). The image enlargement unit 14 generates an observation recorded image by enlarging the acquired captured image (S12). The generated observation recorded image is transmitted to the image filing apparatus 200.

The filtering unit 25 in the image filing apparatus 200 performs band suppression processing on the observation recorded image (S13). The image reducing unit 26 generates an index image by reducing the observation recorded image on which the band suppression processing has been performed (S14). The sharpness correction unit 27 generates a final index image by performing sharpness correction processing on the generated index image (S15).

Figure 15:
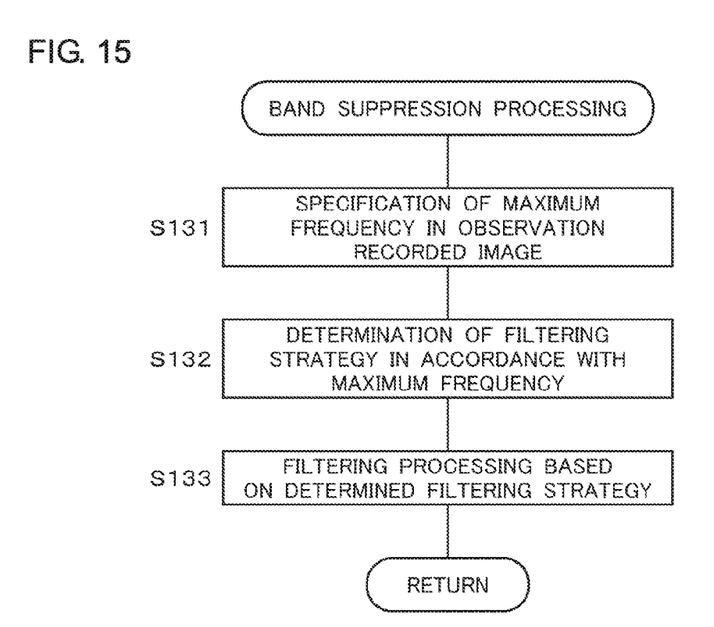
FIG. 15 is a view illustrating a subroutine of Step S13 in the flowchart of FIG. 14.

FIG. 15 illustrates a subroutine of Step S13 in the flowchart of FIG. 14. The filter setting unit 24 specifies a maximum frequency in the observation recorded image based on the number of pixels of the imaging device 51, etc. (S131). The filter setting unit 24 determines a filtering strategy for the observation recorded image in accordance with the specified maximum frequency (S132), and performs filtering processing on the observation recorded image based on the determined filtering strategy (S133).

According to the present embodiment, a low-pass filter to be applied to an observation recorded image can be properly set, as described above. Accordingly, aliasing and excessive smoothing can be prevented, thereby allowing an index image with high-quality to be generated from an observation recorded image.

Additionally, in a process in which multi-stage filters are applied as band suppression processing, the amount of subsequent calculation can be reduced by reducing an image in the middle of the processing, in which the effect of suppressing a high-frequency band component is obtained, with a ratio within a range where aliasing is not caused. A reduction in the calculation amount can save an amount of memory and reduce calculation time. Herein, the reduction processing in the middle of the processing is determined based on the number of times of the application of a filter or on the frequency band suppressed by the application of a filter.

The present invention has been described above based on embodiments. These embodiments are intended to be illustrative only, and it will be obvious to those skilled in the art that various modifications to constituting elements and processes could be developed and that such modifications are also within the scope of the present invention.

In the aforementioned embodiments, an example has been described, in which the function of generating an index image from an observation recorded image is implemented in the image processing unit 23 in the image filing apparatus 200. Regarding this point, the function may be implemented in the image processing unit 13 in the camera control unit 10. In this case, the camera control unit 10 can generate, from a captured image, both an observation recorded image and an index image. Alternatively, the function of generating an index image from an observation recorded image may be implemented in an independent image processing apparatus connected to the camera control unit 10 or the communication line 400.

Although an example, in which a Gaussian filter is used as a low-pass filter, has been described in the aforementioned embodiments, other filters, such as a mean-value filter, may be used.

What is claimed is:
1. An image processing apparatus comprising:
  a processor comprising hardware, wherein the processor is configured to:
    apply a filter for limiting a high-frequency component of a spatial frequency of an image to a second image generated by enlarging an image size of a first image captured by using an endoscope;
    generate a third image by reducing the second image, to which the filter has been applied, to a predetermined image size; and
    set a maximum frequency for band limitation of the filter based on the image size of the first image and the image size of the third image, and further to set both a combination of a first and a second filter coefficients and the number of times of application of the first and the second filter coefficients based on the image size of the first image,
    wherein the first and the second filter coefficients are for determining a frequency characteristic of the filter.

2. The image processing apparatus according to claim 1, wherein the processor is configured to set the maximum frequency for band limitation of the filter based on a ratio of the number of at least either horizontal or vertical pixels of the first image to the number of at least either horizontal or vertical pixels of the third image.

3. The image processing apparatus according to claim 1, wherein the processor is configured to:
   derive a maximum frequency, at which aliasing is not caused in the third image, based on:
      a ratio of the number of at least either horizontal or vertical pixels of the first image to the number of at least either horizontal or vertical pixels of the third image;
      a maximum spatial frequency of an image; and
      a ratio of the number of at least either horizontal or vertical pixels of the first image to the number of at least either horizontal or vertical pixels of the second image; and
   set the maximum frequency as the maximum frequency for band limitation of the filter.

4. The image processing apparatus according to claim 1, wherein the processor is configured to reduce the second image, on which at least one filter operation has been performed, with a reduction ratio within a range where aliasing is not caused, in the middle of a plurality of filter operations.

* * * * *